US00PP14048P39

(12) United States Plant Patent
Kralovetz

(10) Patent No.: US PP14,048 P3
(45) Date of Patent: Aug. 5, 2003

(54) FLORIBUNDA ROSE PLANT NAMED 'KRA BENTIG'

(76) Inventor: Timm R. Kralovetz, 4540 Crowley Dr., Plano, TX (US) 75093

( * ) Notice: Subject to any disclaimer, the term of this patent is extended or adjusted under 35 U.S.C. 154(b) by 0 days.

(21) Appl. No.: 09/917,110

(22) Filed: Jul. 27, 2001

(65) Prior Publication Data

US 2003/0024018 P1 Jan. 30, 2003

(51) Int. Cl.[7] ..... A01H 5/00

(52) U.S. Cl. ..... Plt./143

(58) Field of Search ..... Plt./143, 141, 132

*Primary Examiner*—Bruce R. Campell
*Assistant Examiner*—June Hwu
(74) *Attorney, Agent, or Firm*—Christie, Parker & Hale, LLP

(57) ABSTRACT

A floribunda rose plant producing attractive pink, orange, yellow bi-color flowers and vigorous compact plant with dark green and burgundy foliage.

2 Drawing Sheets

Latin name of genus and species: The present invention relates to a new Rosa hybrida plant.

Variety denomination: The new Rosa hybrida plant has the varietal denomination 'Kra Bentig'.

BACKGROUND OF THE INVENTION

The present invention relates to a new and distinct floribunda rose variety which was originated by my crossing as seed parent the variety known as 'Playboy' (not patented) and as pollen parent the variety known as 'Fragrant Cloud' (U.S. Plant Pat. No. 2,574). The varietal denomination of this new rose is 'Kra Bentig'.

SUMMARY OF THE INVENTION

Among the novel characteristics possessed by the new variety which distinguish it from its parents and all other varieties of which I am aware are its attractive, bi-color flowers.

Asexual reproduction by vegetative cuttings of the new variety as performed in Plano, Tex., shows that the foregoing and other distinguishing characteristics come true to form and are established and transmitted through succeeding propagation. Other known forms of asexual reproduction for roses, may be also employed.

BRIEF DESCRIPTION OF ILLUSTRATIONS

The accompanying photographic illustrations show typical specimens of the vegetative growth and flowers of the new variety in different stages of development and depicted in color as nearly true as it is reasonably possible to make the same in a color illustration of this character.

DESCRIPTION OF THE NEW VARIETY

Figure 1:
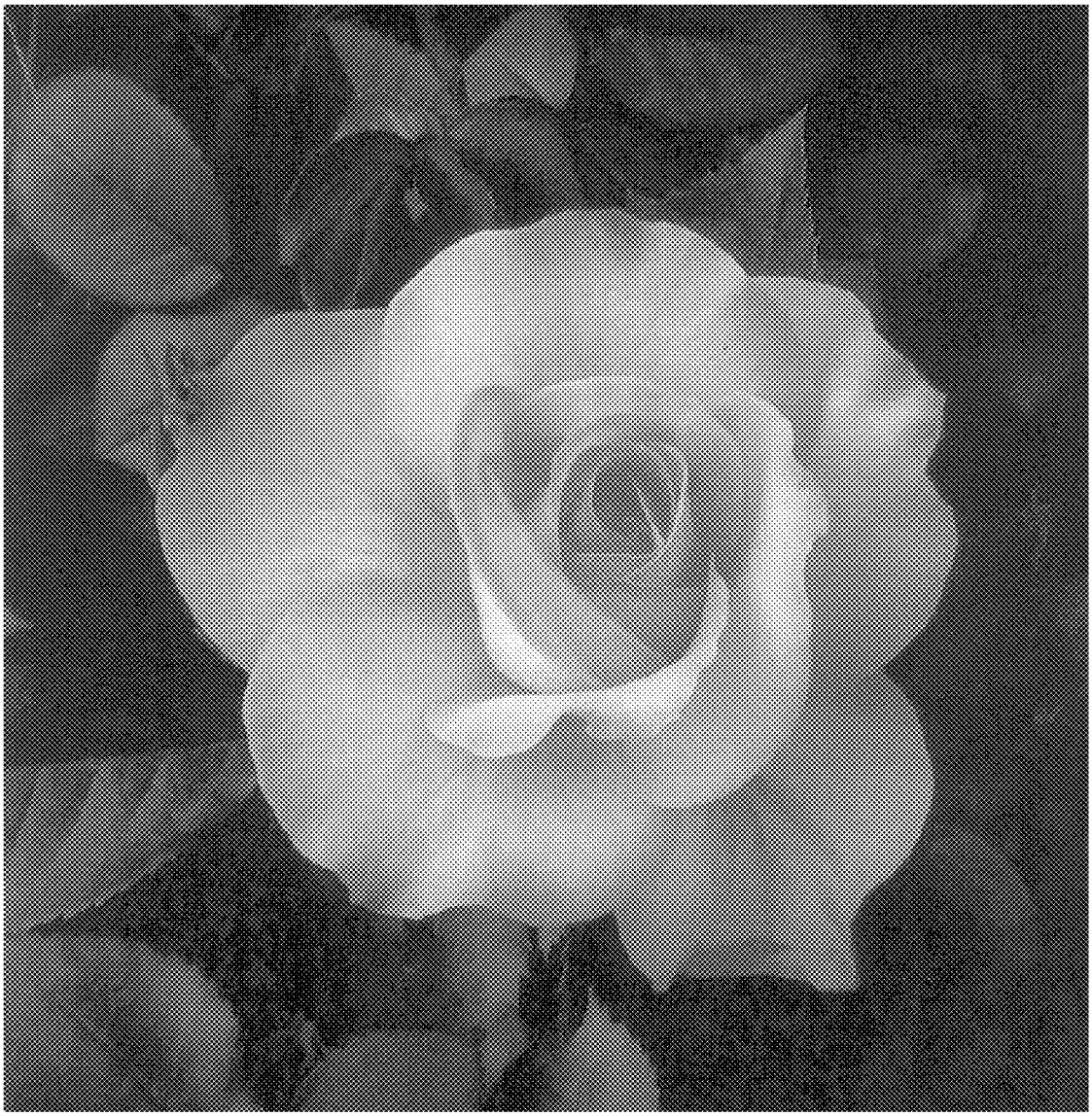
FIG. 1 shows a flower of the new variety.
Figure 2:
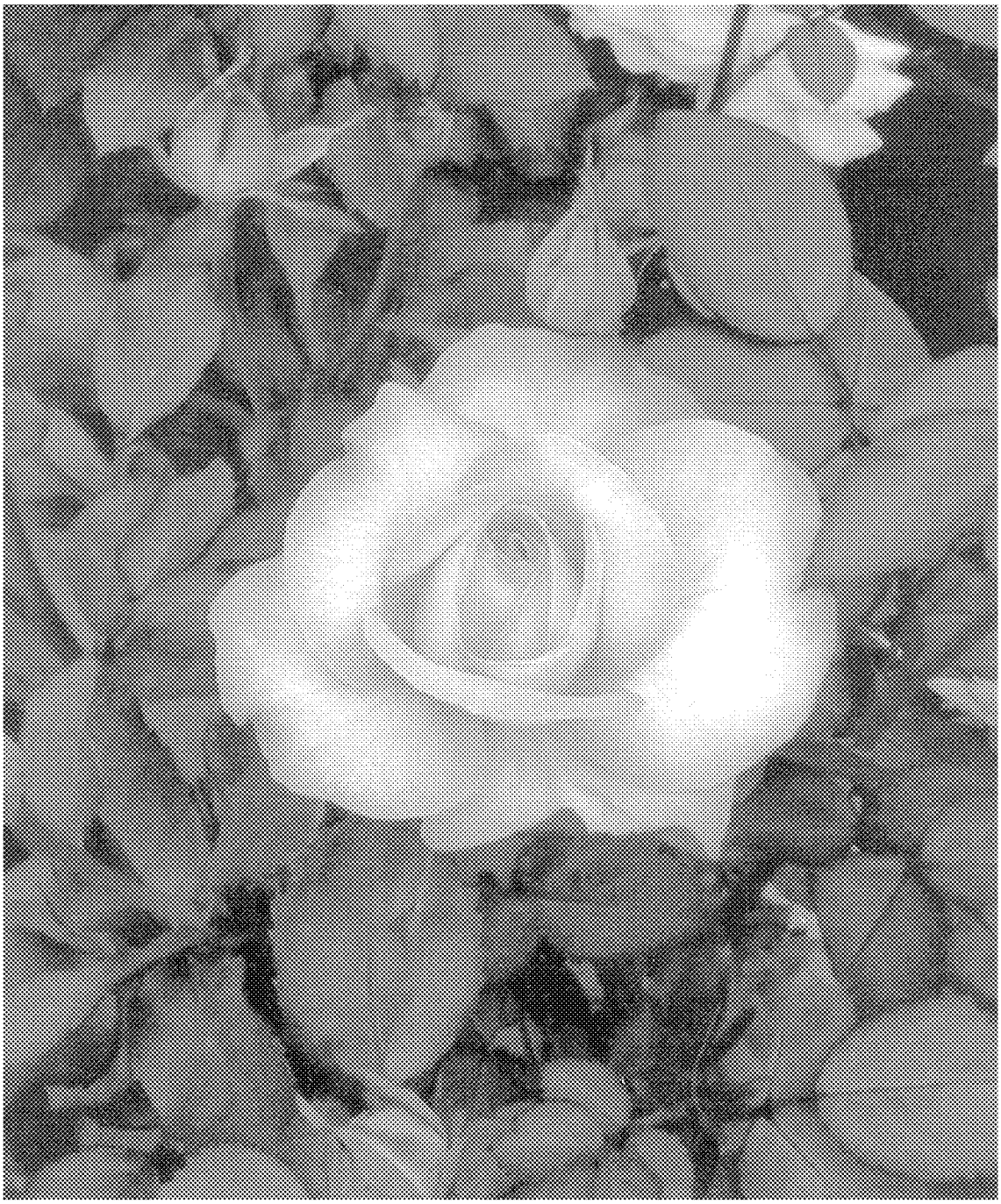
FIG. 2 shows flower and foliage of the new variety.

Parentage: Seedling.
- *Seed parent.*—'Playboy'.
- *Pollen parent.*—'Fragrant Cloud'.

Class: Floribunda.

The following is a detailed description of the new variety, from specimens grown outdoors in Plano, Tex. The color terminology used is in accordance with The Royal Horticultural Society Colour Chart (R.H.S.C.C.), and refers to plate numbers in the aforementioned color chart. Phenotypic expression may vary depending on light, environmental and cultural conditions. In particular, color of foliage and bloom is temperature and light dependent.

FLOWER

Blooming habit: Continuous.

Bud:
- *Size.*—Large, about 1 inch in length, slightly smaller in diameter.
- *Form.*—Pointed.
- *Sepals.*—Long, some sepals foliaceous, sepals cover bud, then divide and fold back at maturity; about 3 to 4 cm in length, with some anthocyanin intonation (reddish-purple) on the outer surfaces and foliaceous appendages; upper surface smooth and glossy; lower surface smooth.
- *Color.*—Near 74B to 74C at upper portion to near 11C to 11D toward base.
- *Peduncle.*—Length: About 9 cm to about 12 cm. Aspect: Rough. Strength: Erect, sturdy. Color: Near 187B. Surface texture: Smooth.
- *Bracts.*—Near 137A.

Bloom:
- *Size.*—Average size when fully expanded — about 3–4 inches.
- *Borne.*—Singly and in clusters of three.
- *Form.*—High centered, exhibition type at first; petals imbricated.
- *Petalage.*—Number of petals under normal conditions — about 30 to 36.

Color (⅓ to ½ open):
- *Top surface.*—Outer edge from near 66D to near 66B; center portion white, 155C with lower portion of petal near 19B to 19C.
- *Under surface.*—Outer edge near 69C washing into near 19C.
- *Center.*—Color where petals bunch near 38A.

General tonality from a distance: Attractive plant, bi-color mango, yellow.

Petals:

*Texture.*—Medium thick, smooth.

*Appearance.*—Inside slightly matte and outside matte.

*Form.*—Orbicular, fan-shaped with rounded apices; margin entire.

*Arrangement.*—Imbricated.

*Petaloids.*—Few, from 2 to 4; average size about. ¼-inch, crinkly shape with color same as petal.

*Persistence.*—Petals drop off cleanly.

*Fragrance.*—Light to moderate.

Receptacle: Small, less than ½-inch in length; yellow-green, 155B and somewhat flat to round in form.

Hips: Present; green and somewhat flat to round in form.

Reproductive organs: Anther color yellow-orange and pistil color yellow.

Lastingness of bloom: About 3 to 9 days on the bush, depending on temperature; about 3–4 days cut flower.

PLANT

Form: Small to compact, growing to about 4 ft by 4 ft bush.

Growth: Vigorous.

Foliage: Compound leaf, 3 to 5 leaflets.

*Size.*—Medium, about 1-inch in length, ¾-inch in widths.

*Quantity.*—Abundant.

*Color.*—New foliage: Green, near 138A to 138B, may have Burgundy, near 187B, cast expressly at some edges. Mature foliage: Greyed green, near 189A, with Burgundy, near 187B, cast expressly at some edges; underside similar coloring; foliage may turn burgundy, near 187B, with cooler temperatures.

*Shape.*—Ovate.

*Texture.*—Upper side: leathery, semi-glossy. Under side: leathery.

*Edge.*—Serrated.

*Serration.*—Serrate.

*Leaf stem.*—Color — green, near 143C, in younger leaves to greyed red, near 182A, in mature leaves.

*Leaf apex.*—Acute .

*Leaf base.*—Obtuse.

Stipule: About ¼-inch, yellow green in color, near 145A.

Rachis: Smooth, light green in color, near 145B.

Resistance to disease: Very resistant to mildew, rust and blackspot.

WOOD

Color: Near 187A to 187D tinged with green, 146B bark smooth.

Flower stem: About 4 to 11 inches from last cut.

Thorns:

*Quantity, color, shape and size.*—Few, mature thorns dark red, near 185A; shape linear, with downward hook; length about 5/16-inch.

*Hardiness.*—Has survived 24° F. to 106° F.

I claim:

1. A new and distinct floribunda rose plant, substantially as shown and described.

* * * * *